(12) United States Patent
Hu et al.

(10) Patent No.: US 11,961,609 B2
(45) Date of Patent: Apr. 16, 2024

(54) 3D IMAGE CLASSIFICATION METHOD AND APPARATUS, DEVICE, AND STORAGE MEDIUM

(71) Applicant: TENCENT TECHNOLOGY (SHENZHEN) COMPANY LIMITED, Guangdong (CN)

(72) Inventors: Yi Fan Hu, Shenzhen (CN); Ye Feng Zheng, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 403 days.

(21) Appl. No.: 17/383,724

(22) Filed: Jul. 23, 2021

(65) Prior Publication Data

US 2021/0350187 A1    Nov. 11, 2021

Related U.S. Application Data

(63) Continuation of application No. PCT/CN2020/097530, filed on Jun. 22, 2020.

(30) Foreign Application Priority Data

Jun. 27, 2019 (CN) .......................... 201910568666.X

(51) Int. Cl.
*G06V 10/764* (2022.01)
*G06F 18/21* (2023.01)
(Continued)

(52) U.S. Cl.
CPC ........... *G16H 30/40* (2018.01); *G06F 18/214* (2023.01); *G06F 18/217* (2023.01); *G06F 18/24* (2023.01);
(Continued)

(58) Field of Classification Search
CPC .. G06V 10/454; G06V 10/764; G06V 10/806; G06V 10/82; G06V 2201/03
See application file for complete search history.

(56) References Cited

U.S. PATENT DOCUMENTS 6,415,048 B1    7/2002  Schneider
6,731,283 B1    5/2004  Navab
(Continued)

FOREIGN PATENT DOCUMENTS

CN          101615289 A        12/2009
CN          108294780 A         7/2018
(Continued)

OTHER PUBLICATIONS

International Search Report for PCT/CN2020/097530 dated Sep. 27, 2020 (PCT/ISA/210).
(Continued)

*Primary Examiner* — Ming Y Hon
(74) *Attorney, Agent, or Firm* — Sughrue Mion, PLLC

(57) ABSTRACT

The disclosure provides a three-dimensional (3D) image classification method and apparatus, a device, and a storage medium. The method includes: obtaining a 3D image, the 3D image including first-dimensional image information, second-dimensional image information, and third-dimensional image information; extracting a first image feature corresponding to planar image information from the 3D image; extracting a second image feature corresponding to the third-dimensional image information from the 3D image; fusing the first image feature and the second image feature, to obtain a fused image feature corresponding to the 3D image; and determining a classification result corresponding to the 3D image according to the fused image feature corresponding to the 3D image.

20 Claims, 9 Drawing Sheets

(51) Int. Cl.
| | |
|---|---|
| *G06F 18/214* | (2023.01) |
| *G06F 18/24* | (2023.01) |
| *G06F 18/25* | (2023.01) |
| *G06N 3/08* | (2023.01) |
| *G06V 10/44* | (2022.01) |
| *G06V 10/80* | (2022.01) |
| *G06V 10/82* | (2022.01) |
| *G16H 30/20* | (2018.01) |
| *G16H 30/40* | (2018.01) |

(52) U.S. Cl.
CPC ............ *G06F 18/253* (2023.01); *G06N 3/08* (2013.01); *G06V 10/454* (2022.01); *G06V 10/764* (2022.01); *G06V 10/806* (2022.01); *G06V 10/82* (2022.01); *G16H 30/20* (2018.01); *G06V 2201/03* (2022.01)

(56) References Cited

U.S. PATENT DOCUMENTS

| | | | | |
|---|---|---|---|---|
| 9,968,257 | B1* | 5/2018 | Burt | ............... A61B 5/0035 |
| 11,769,110 | B1* | 9/2023 | Bourke | ............ G06Q 10/0631 |
| | | | | 705/28 |
| 2015/0302572 | A1* | 10/2015 | Georgeson | ............. G06T 7/001 |
| | | | | 382/202 |
| 2018/0156713 | A1* | 6/2018 | Berezhna | ............... G02B 7/365 |
| 2020/0302149 | A1* | 9/2020 | Gottemukkula | ....... G06N 3/084 |
| 2020/0364856 | A1* | 11/2020 | Nicolaes | ............... G06T 7/0012 |
| 2020/0401854 | A1* | 12/2020 | Peng | ................... G06F 18/2148 |
| 2021/0049397 | A1* | 2/2021 | Chen | ..................... G06V 10/30 |
| 2021/0133977 | A1* | 5/2021 | Yamazaki | ................ G06T 7/11 |
| 2021/0158526 | A1* | 5/2021 | Patil | ..................... A61B 5/055 |
| 2021/0209426 | A1* | 7/2021 | Jia | ........................... G06F 18/21 |
| 2022/0019870 | A1* | 1/2022 | Gu | ........................ G06N 3/045 |
| 2023/0293995 | A1* | 9/2023 | Zhang | ..................... A63F 13/52 |
| | | | | 463/31 |
| 2023/0298356 | A1* | 9/2023 | Vora | ..................... G06V 20/70 |
| | | | | 382/103 |

FOREIGN PATENT DOCUMENTS

| | | |
|---|---|---|
| CN | 108960322 A | 12/2018 |
| CN | 110276408 A | 9/2019 |

OTHER PUBLICATIONS

Written Opinion of the International Searching Authority for PCT/CN2020/097530 dated Sep. 27, 2020 (PCT/ISA/237).

* cited by examiner

3D IMAGE CLASSIFICATION METHOD AND APPARATUS, DEVICE, AND STORAGE MEDIUM

CROSS-REFERENCE TO RELATED APPLICATION(S)

This application is a continuation application of International Application No. PCT/CN2020/097530, filed on Jun. 22, 2020, which claims priority to Chinese Patent Application No. 201910568666.X filed with the China National Intellectual Property Administration on Jun. 27, 2019, the disclosures of which are incorporated by reference in their entireties.

FIELD

Embodiments of the disclosure relate to the field of deep learning technologies, and in particular, to a three-dimensional (3D) image classification method and apparatus, a device, and a storage medium.

BACKGROUND

A medical image is an image that is obtained non-invasively from a human body or a part of a human body and that is generated by a medical instrument in internal tissue imaging technologies and processing operations. Because a human body and a human body lesion are three-dimensional (3D) structures, many effective medical images are 3D images.

Currently, it is typical that a doctor performs etiological diagnosis by using a medical image. During etiological diagnosis by using a medical image, a classification result of the medical image needs to be determined. In the related art, a classification result of a medical image is generally determined by a doctor based on knowledge, experience, and the like of the doctor.

Thus, in the related art, a classification result of a medical image is manually determined, which causes problems of low efficiency and low accuracy.

SUMMARY

Embodiments of the disclosure provide a three-dimensional (3D) image classification method and apparatus, a device, and a storage medium, to improve efficiency and accuracy in determining of a classification result of a 3D image.

According to an aspect, an embodiment of the disclosure provides a 3D image classification method, applicable to a computer device, the method including:
  obtaining a 3D image, the 3D image including first-dimensional image information, second-dimensional image information, and third-dimensional image information;
  extracting a first image feature corresponding to planar image information from the 3D image, the planar image information including the first-dimensional image information and the second-dimensional image information;
  extracting a second image feature corresponding to the third-dimensional image information from the 3D image;
  fusing the first image feature and the second image feature, to obtain a fused image feature corresponding to the 3D image; and
  determining a classification result corresponding to the 3D image according to the fused image feature corresponding to the 3D image.

According to another aspect, an embodiment of the disclosure provides a 3D image classification apparatus, including at least one memory configured to store program code; and at least one processor configured to read the program code and operate as instructed by the program code, the program code including:
  image obtaining code configured to cause the at least one processor to obtain a 3D image, the 3D image including first-dimensional image information, second-dimensional image information, and third-dimensional image information;
  first extraction code configured to cause the at least one processor to extract a first image feature corresponding to planar image information from the 3D image, the planar image information including the first-dimensional image information and the second-dimensional image information;
  second extraction code configured to cause the at least one processor to extract a second image feature corresponding to the third-dimensional image information from the 3D image;
  feature fusion code configured to cause the at least one processor to fuse the first image feature and the second image feature, to obtain a fused image feature corresponding to the 3D image; and
  image classification code configured to cause the at least one processor to determine a classification result corresponding to the 3D image according to the fused image feature corresponding to the 3D image.

According to still another aspect, an embodiment of the disclosure provides a computer device, including a processor and a memory, the memory storing at least one instruction, at least one program, a code set, or an instruction set, and the at least one instruction, the at least one program, the code set, or the instruction set being loaded and executed by the processor to implement the 3D image classification method according to one of the foregoing aspects.

According to still another aspect, an embodiment of the disclosure provides a non-transitory computer-readable storage medium, storing at least one instruction, at least one program, a code set, or an instruction set, the at least one instruction, the at least one program, the code set, or the instruction set being loaded and executed by a processor to implement the 3D image classification method according to one or more of the foregoing aspects.

According to still another aspect, a computer program product is provided, when executed, the computer program product being used for performing the 3D image classification method according to one or more of the foregoing aspects.

BRIEF DESCRIPTION OF THE DRAWINGS

Aspects of the disclosure will be more apparent by describing certain example embodiments with reference to the accompanying drawings.

DETAILED DESCRIPTION

To make the objectives, technical solutions, and advantages of the disclosure clearer, the following further describes example implementations of the disclosure in detail with reference to the accompanying drawings.

Figure 1:
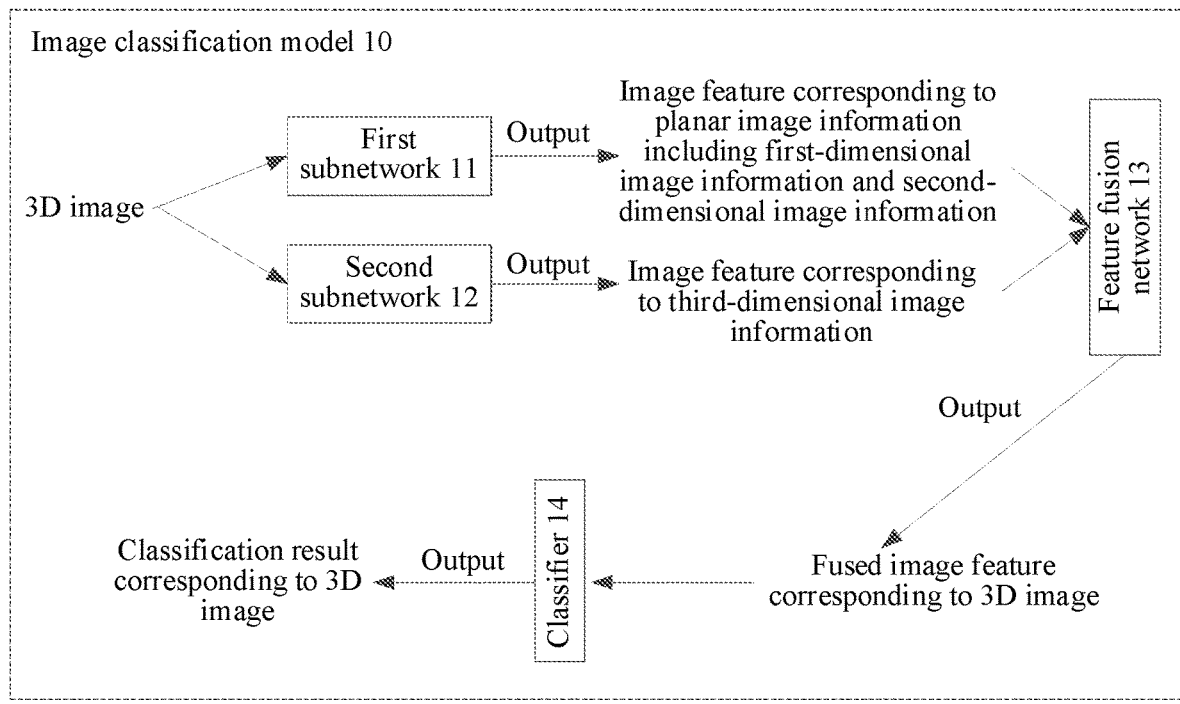
FIG. 1 is a schematic structural diagram of an image classification model according to an embodiment of the disclosure.

FIG. 1 is a schematic diagram of an image classification model according to an embodiment of the disclosure. The image classification model 10 includes a first subnetwork 11, a second subnetwork 12, a feature fusion network 13, and a classifier 14.

The first subnetwork 11 is configured to extract, from a three-dimensional (3D) image, a first image feature corresponding to planar image information including first-dimensional image information and second-dimensional image information. Specifically, the first subnetwork 11 extracts the first image feature through the following operations: compressing third-dimensional image information in the 3D image, to obtain a first processing result; performing channel expansion on the first processing result, to obtain a second processing result; setting a weight for image information of at least one region in the second processing result, to obtain a third processing result, the at least one region being a region in a plane including a first dimension and a second dimension; and performing feature extraction on the third processing result, to obtain the first image feature. The first subnetwork 11 may alternatively be referred to as a slow branch.

Figure 2:
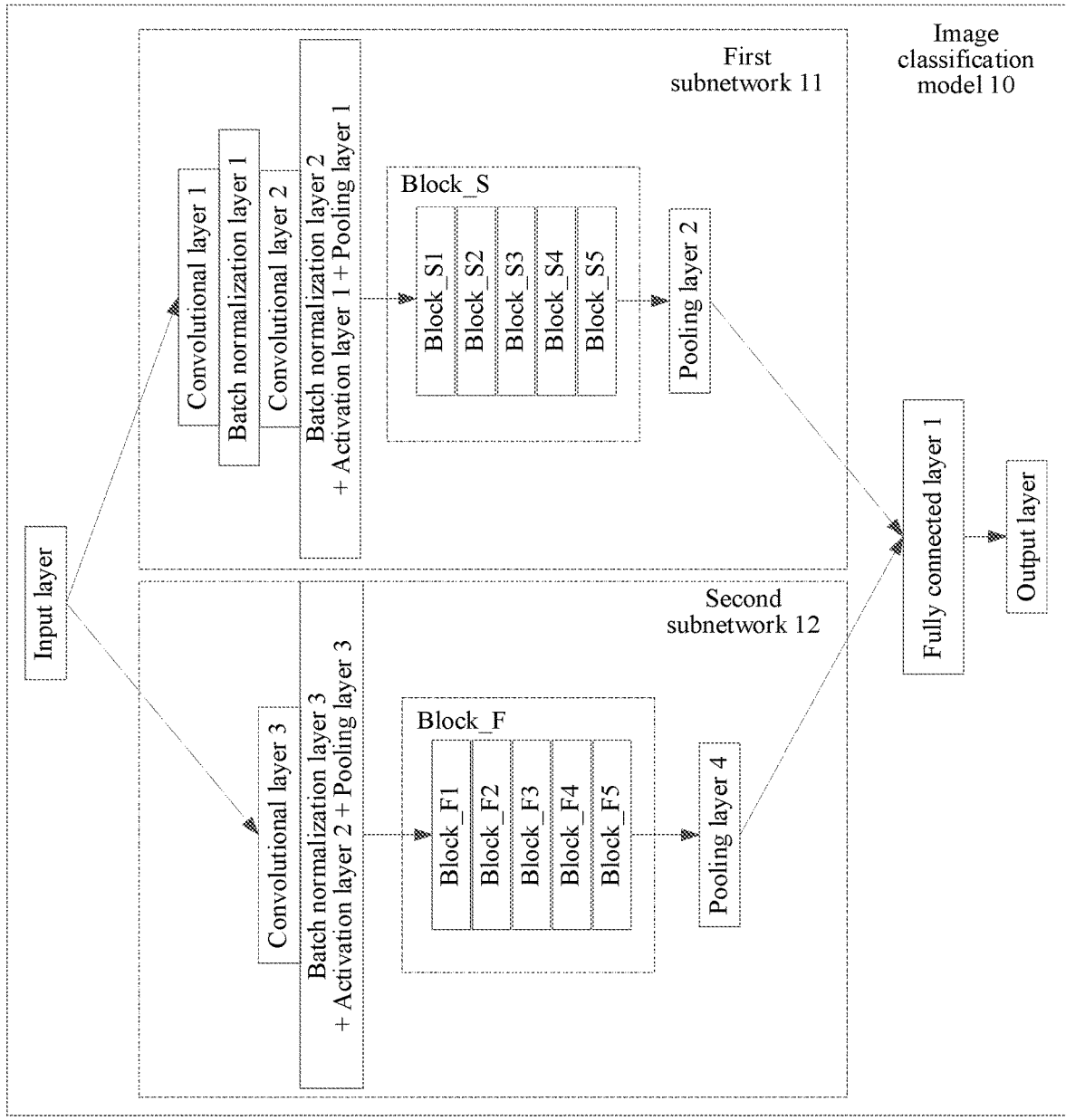
FIG. 2 is a schematic structural diagram of an image classification model according to another embodiment of the disclosure.

Referring to FIG. 2, the first subnetwork 11 includes a two-layer network structure, which includes convolutional layer 1 and a batch normalization (BN) layer 1. The two-layer network structure implements the foregoing operation of compressing third-dimensional image information in the 3D image, to obtain a first processing result. The first subnetwork 11 further includes a four-layer network structure, which includes a convolutional layer 2, a BN layer 2, an activation layer 1, and a pooling layer 1. The four-layer network structure implements the foregoing operation of performing channel expansion on the first processing result, to obtain a second processing result. The activation layer is configured to perform non-linear activation processing; and the pooling layer is configured to perform max-pooling processing. The first subnetwork 11 further includes a Block_S layer (including Block_S1, Block_S2, Block_S3, Block_S4, and Block_S5). The Block_S layer implements the foregoing operations of setting a weight for image information of at least one region in the second processing result, to obtain a third processing result; and performing feature extraction on the third processing result, to obtain the first image feature. The first subnetwork further includes a pooling layer 2. The pooling layer 2 is configured to perform average pooling processing.

Figure 3:
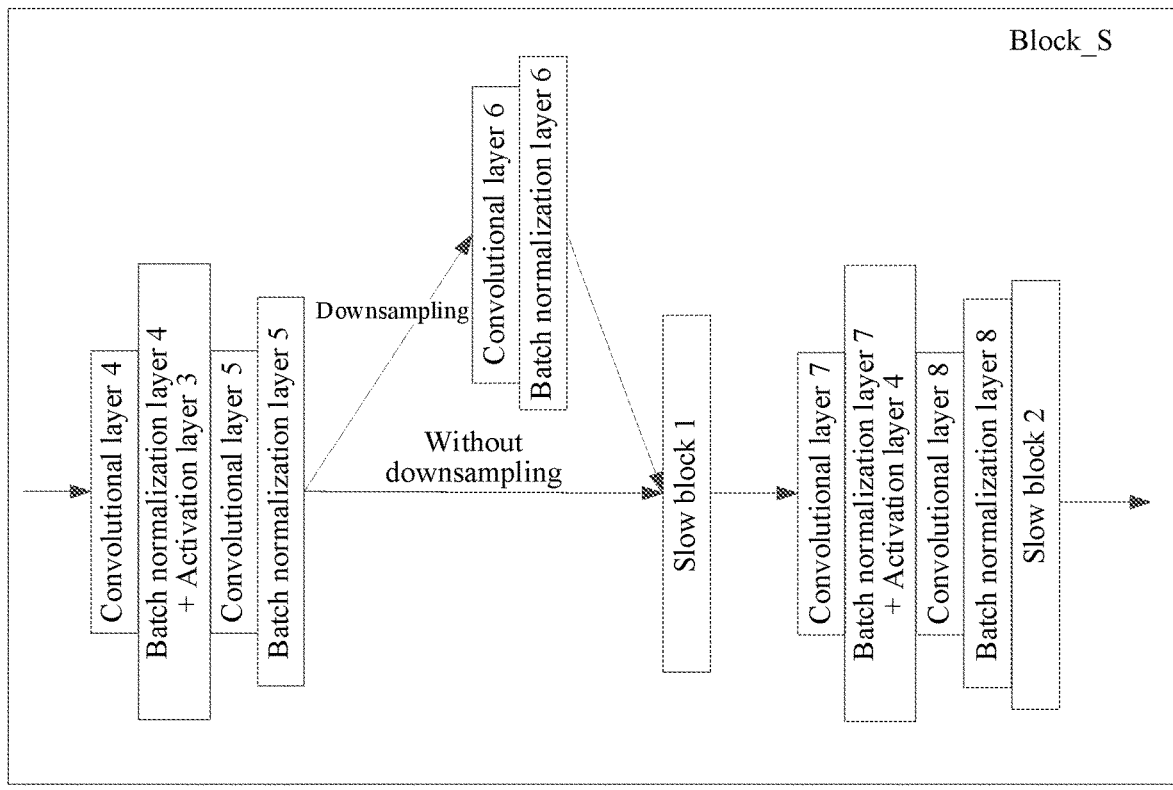
FIG. 3 is a schematic structural diagram of a Block_S layer according to an embodiment of the disclosure.

FIG. 3 shows a schematic structural diagram of a Block_S layer according to an embodiment of the disclosure. In an example, the Block_S layer includes a convolutional layer 4, a BN layer 4, an activation layer 3, a convolutional layer 5, a BN layer 5, a convolutional layer 6, a BN layer 6, a slow block 1, a convolutional layer 7, a BN layer 7, an activation layer 4, a convolutional layer 8, a BN layer 8, and a slow block 2. After being downsampled, output data of the BN layer 5 is inputted into the convolutional layer 6, and is finally inputted into the slow block 1 from the BN layer 6. In addition, the output data of the BN layer 5 is directly inputted into the slow block 1 without being downsampled. In addition, the slow block 1 and the slow block 2 are configured to implement the foregoing operation of setting a weight for image information of at least one region in the second processing result, to obtain a third processing result.

Figure 5:
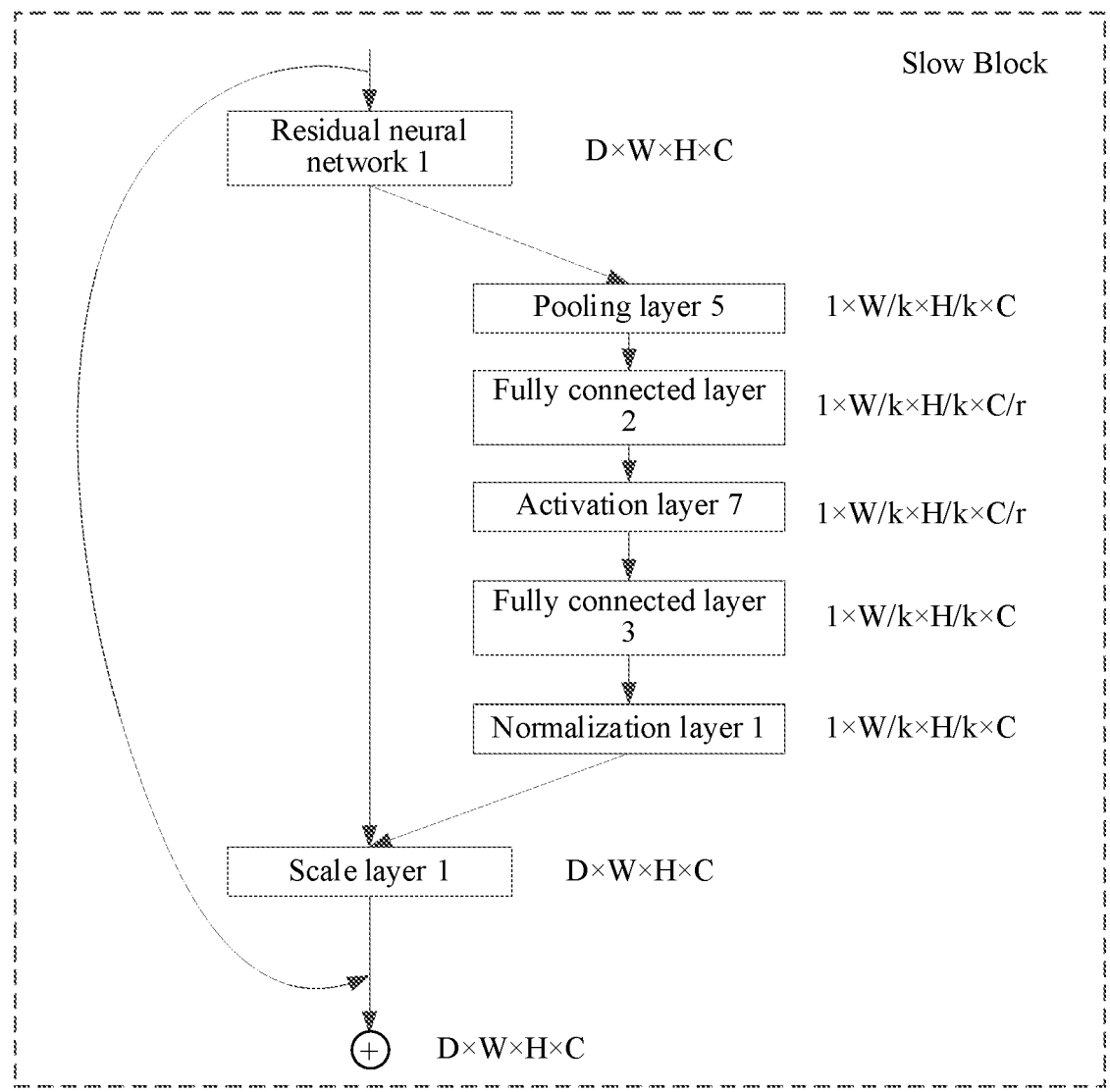
FIG. 5 is a schematic structural diagram of a slow block according to an embodiment of the disclosure.

FIG. 5 shows a schematic structural diagram of a slow block (e.g., a slow block 1 or a slow block 2) according to an embodiment of the disclosure. In an example, the slow block includes a residual neural network 1, a pooling layer 5, a fully connected (FC) layer 2, an activation layer 7, a FC layer 3, a normalization layer 1, and a scale layer 1. For a connection sequence of the foregoing layers, reference may be made to FIG. 5. Output data of the residual neural network 1 is inputted into the pooling layer 5, and after a series of processing, the output data is inputted into the scale layer 1. In addition, the output data of the residual neural network 1 is further directly inputted into the scale layer 1. In addition, starting from the pooling layer 5, the plane including the first dimension and the second dimension are divided into k×k regions, and then weights are respectively set for the k×k regions. D in FIG. 5 represents a third dimension, W represents the first dimension, H represents the second dimension, and C represents a channel.

The second subnetwork 12 is configured to extract the second image feature corresponding to the third-dimensional image information from the 3D image. Specifically, the second subnetwork 12 extracts the second image feature through the following operations: performing channel expansion on the 3D image, to obtain a fourth processing result; setting a weight for at least one channel in the fourth processing result, to obtain a fifth processing result; and performing feature extraction on the fifth processing result, to obtain the second image feature. The second subnetwork 12 may alternatively be referred to as a fast branch. Referring to FIG. 2, the second subnetwork 12 includes a four-layer network structure, which includes a convolutional layer 3, a BN layer 3, an activation layer 2, and a pooling layer 3. The four-layer network structure implements the foregoing operation of performing channel expansion on the 3D image, to obtain a fourth processing result. The activation layer is configured to perform non-linear activation processing; and the pooling layer is configured to perform max-pooling processing. The second subnetwork 12 further includes a Block_F layer (including Block_F1, Block_F2, Block_F3, Block_F4, and Block_F5). The Block_F layer implements the foregoing operations of setting a weight for at least one channel in the fourth processing result, to obtain a fifth processing result; and performing feature extraction on the fifth processing result, to obtain the second image feature. The second subnetwork 12 further includes a pooling layer 4. The pooling layer 4 is configured to perform average pooling processing.

Figure 4:
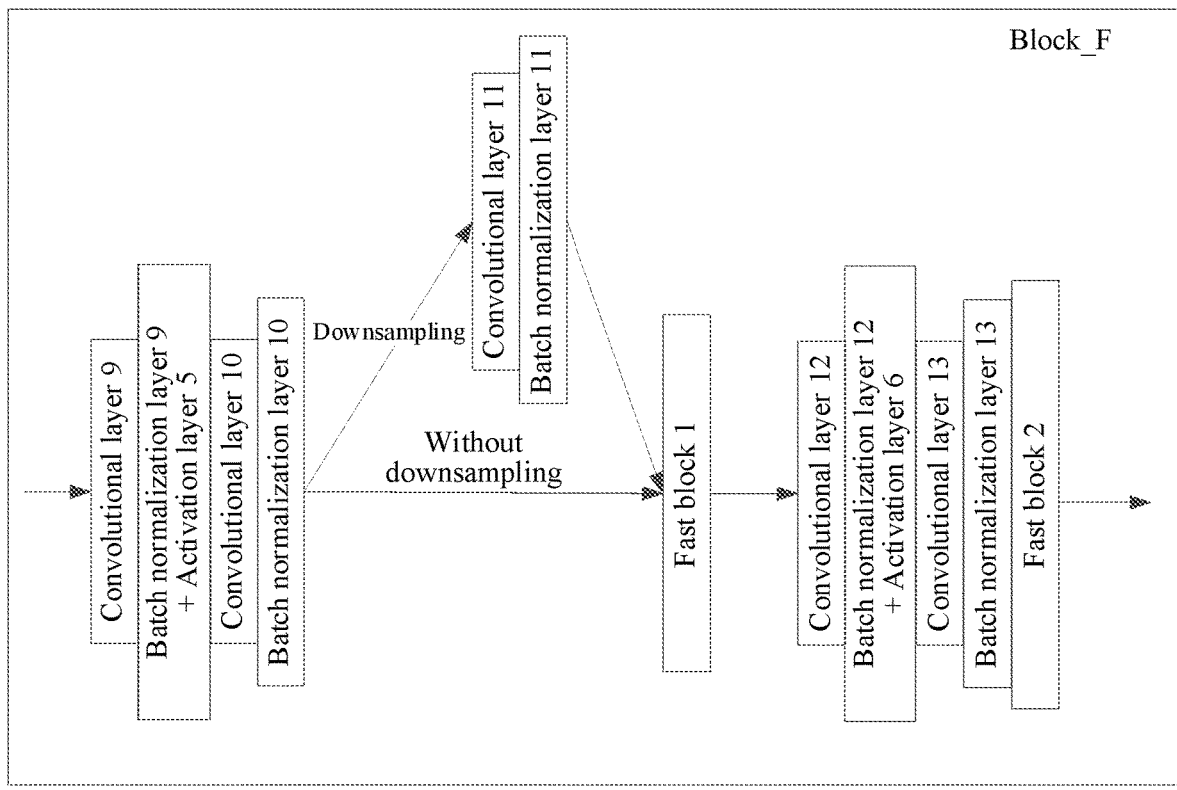
FIG. 4 is a schematic structural diagram of a Block_F layer according to an embodiment of the disclosure.

FIG. 4 shows a schematic structural diagram of a Block_F layer according to an embodiment of the disclosure. In an example, the Block_F layer includes a convolutional layer 9, a BN layer 9, an activation layer 5, a convolutional layer 10, a BN layer 10, a convolutional layer 11, a BN layer 11, a fast block 1, a convolutional layer 12, a BN layer 12, an activation layer 6, a convolutional layer 13, a BN layer 13, and a fast block 2. For a connection sequence of the foregoing layers, reference may be made to FIG. 4. After being downsampled, output data of the BN layer 9 is inputted into the convolutional layer 10, and is finally inputted into the fast block 1 from the BN layer 10. In addition, the output data of the BN layer 10 is directly inputted into the fast block 1 without being downsampled. In addition, the fast block 1 and the fast block 2 are configured to implement the foregoing operation of setting a weight for at least one channel in the fourth processing result, to obtain a fifth processing result.

Figure 6:
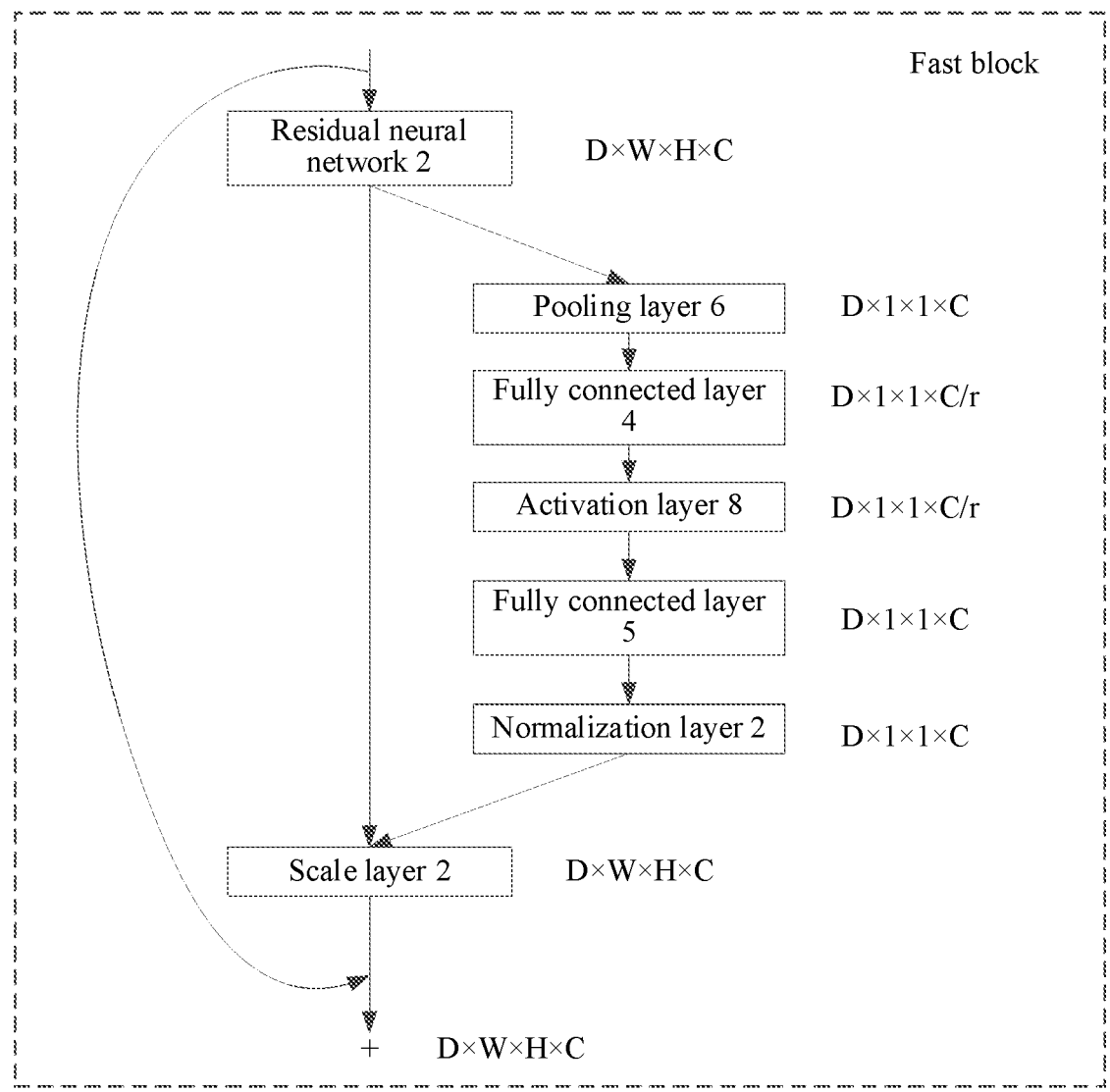
FIG. 6 is a schematic structural diagram of a fast block according to an embodiment of the disclosure.

FIG. 6 shows a schematic structural diagram of a fast block (e.g., a fast block 1 or a fast block 2) according to an embodiment of the disclosure. In an example, the fast block includes a residual neural network 2, a pooling layer 6, an FC layer 4, an activation layer 8, an FC layer 5, a normalization layer 2, and a scale layer 2. For a connection sequence of the foregoing layers, reference may be made to FIG. 6. Output data of the residual neural network 2 is inputted into the pooling layer 6, and after a series of processing, the output data is inputted into the scale layer 2. In addition, the output data of the residual neural network 2 is further directly inputted into the scale layer 2. In addition, starting from the pooling layer 6, a computer device sets a weight for each feature channel.

The feature fusion network 13 is configured to fuse the first image feature and the second image feature, to obtain the fused image feature corresponding to the 3D image. Referring to FIG. 2, the feature fusion network includes an FC layer 1. The FC layer 1 is configured to fuse the first image feature and the second image feature, to obtain the fused image feature corresponding to the 3D image. In addition, an input layer and an output layer are further included in FIG. 2. The classifier 14 is configured to classify the fused image feature corresponding to the 3D image, to obtain a classification result corresponding to the 3D image.

In the related art, there are 3D images with resolutions varying in planes. An example in which the 3D image is a medical image is used. The medical image is obtained by scanning a human body or a tissue of a human body layer by layer. A medical instrument obtains one two-dimensional (2D) image (for example, an x-y plane) by scanning each layer, and a plurality of layers of 2D images are superimposed to obtain a 3D image. In this way, a resolution in the x-y plane is relatively high, and a resolution in a plane including a z direction is relatively low. When images of this type are used as a whole for feature extraction, impact of different resolutions in different planes cannot be taken into consideration. Consequently, an extracted feature is not sufficiently high quality and accuracy in subsequent image classification is relatively low.

In the technical solutions provided in the embodiments of the disclosure, for a 3D image, an image classification model respectively extracts an image feature corresponding to planar image information (for example, x-y planar image information) including first-dimensional image information and second-dimensional image information and an image feature corresponding to third-dimensional image information (for example, z-direction image information), then fuses the two extracted features, to obtain a fused image feature, and determines a classification result corresponding to the 3D image by using the fused image feature. Compared with manually determining a classification result of a 3D image in the related art, the disclosure may improve efficiency and accuracy in image classification. In addition, because the image feature corresponding to the x-y planar image information and the image feature corresponding to the z-direction image information are respectively extracted in two manners, interference caused by different resolutions of the 3D image in different planes may be avoided. Therefore, finer and richer features are extracted, which improves accuracy in image classification.

The technical solutions provided in the embodiments of the disclosure may be applied to the medical field, that is, classification on medical images. Specifically, the computer device inputs a medical image into an image classification model. The image classification model extracts an image feature corresponding to x-y planar image information and an image feature corresponding to z-direction image information, fuses the two image features to obtain a fused image feature, finally performs classification according to the fused image feature, and determines a disease type or a cause of disease according to a classification result.

The technical solutions provided in the embodiments of the disclosure may be applied to a computer device. An image classification model is configured in the computer device. The computer device may be a terminal device such as a smartphone, a personal computer, or a tablet computer, or may be a server.

Figure 7:
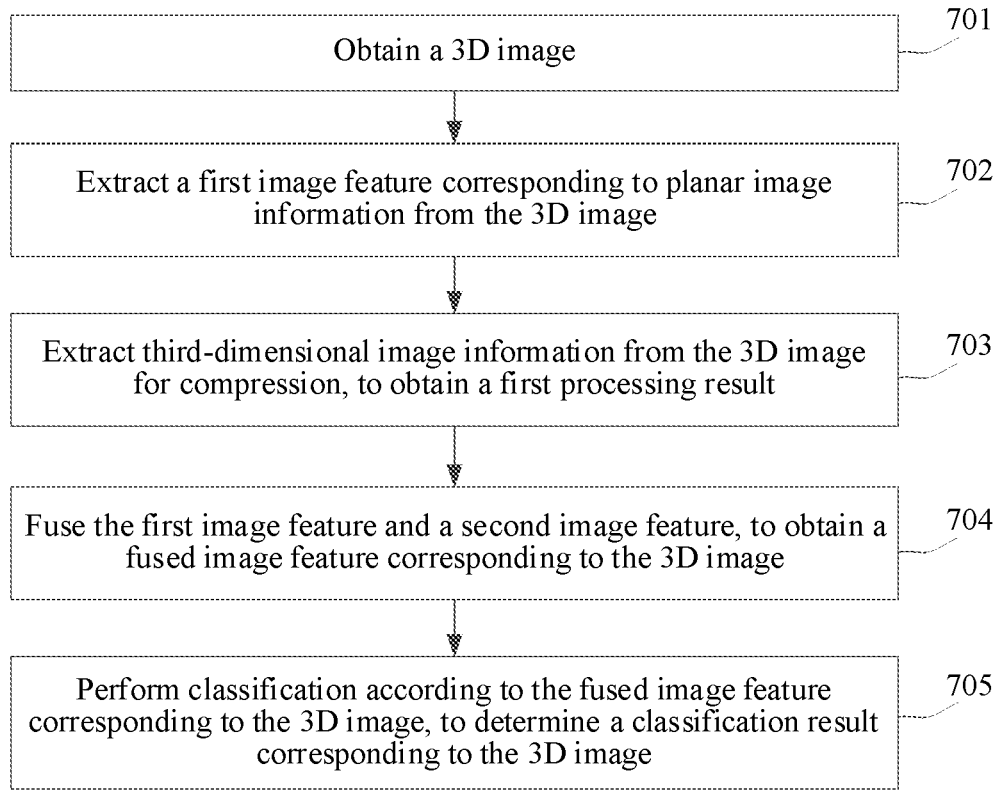
FIG. 7 is a flowchart of a 3D image classification method according to an embodiment of the disclosure.

FIG. 7 is a flowchart of a 3D image classification method according to an embodiment of the disclosure. The method includes the following operations 701-705:

Operation 701: Obtain a 3D image.

The 3D image refers to an image having a 3D effect. In an example embodiment of the disclosure, the 3D image includes first-dimensional image information, second-dimensional image information, and third-dimensional image information. In an example embodiment, the first dimension, the second dimension, and the third dimension are represented by using x, y, and z in a 3D coordinate system.

The 3D image may be a medical image, or may be a frame of image in a 3D video. In an example embodiment of the disclosure, for illustrative purposes, a description is made by using an example in which the 3D image is a medical image. The medical image is obtained by scanning a human body or a tissue of a human body layer by layer. A medical instrument obtains one 2D image by scanning each layer, and a plurality of layers of 2D images are superimposed to obtain a 3D image. The 2D image includes first-dimensional image information and second-dimensional image information, and image information obtained along a superimposition direction is third-dimensional image information. In an example embodiment of the disclosure, the computer device may be connected to the medical instrument, and then obtains the 3D image from the medical instrument.

In addition, when the 3D image is a medical image, before the medical image is classified, the medical image may be pre-processed. The pre-processing may include the following: a pathological region is annotated in the medical image, to obtain an annotated medical image, and subsequently, the image classification model is configured to classify the annotated medical image.

In an example embodiment, the medical image is in an editable state, and the computer device receives an annotation signal acting on the medical image, to obtain an annotated medical image. The annotation signal may be triggered by a doctor. After determining a region in the medical image as a pathological region, the doctor may frame the region, to annotate the medical image. In another example embodiment, a positioning model is further configured in the computer device. The positioning model outputs a position in which the pathological region is located in the medical image, to obtain an annotated medical image. The positioning model is obtained by training a neural network by using a medical sample image annotated with a pathological region.

When a lesion occurs on a human body or a tissue of a human body, a region in which the lesion occurs is scanned by using a medical instrument, to obtain a pathological region. A main objective of classifying a medical image is to determine a disease type (or make a diagnosis). In an example embodiment of the disclosure, a pathological region is annotated in the medical image, and during subsequent feature extraction, the image classification model only needs to perform feature extraction on the pathological region, thereby reducing workloads when the image classification model performs feature extraction, and improving efficiency in classification.

In an example embodiment, before performing feature extraction, the computer device may further detect whether a case in which resolutions in two planes are different exists in the 3D image. If the case exists, subsequent operations 702 to 705 are performed; and if the case does not exist, it is unnecessary to perform the subsequent operations 702 to 705, and image features corresponding to the 3D image may be directly extracted. In the foregoing manner, execution of the operation of feature fusion may be omitted, thereby improving efficiency in classification.

Operation 702: Extract a first image feature corresponding to planar image information from the 3D image.

The planar image information includes first-dimensional image information and second-dimensional image information. In an example embodiment of the disclosure, the image classification model extracts the first image feature from the 3D image. The image classification model is obtained by training a neural network model by using a 3D sample image annotated with an expected classification result. A neural network may be a convolutional neural network (CNN), an artificial neural network (ANN), a deep neural network (DNN), or the like. This is not limited in an example embodiment of the disclosure. A machine learning algorithm used during training of a machine learning model may be a back-propagation (BP) algorithm, a faster regions with convolutional neural network (faster RCNN) algorithm, or the like. This is not limited in an example embodiment of the disclosure. For example structures of the image classification model and functions implemented by the structures, reference may be made to FIG. 1 to FIG. 6 and related descriptions. Details are not described herein again.

In an example embodiment, the planar image information including the first-dimensional image information and the second-dimensional image information is x-y planar image information. In an example embodiment, operation 702 includes the following sub operations:

Suboperation 702a: Compress third-dimensional image information in the 3D image, to obtain a first processing result.

The computer device inputs the 3D image into the image classification model. Before extracting the first image feature, the image classification model compresses the third-dimensional image information, to reduce an information volume of the third-dimensional image information. Subsequently, when the first image feature corresponding to the planar image information including the first-dimensional image information and the second-dimensional image information is extracted, interference caused by the third-dimensional image information may be reduced, and finally, the first processing result is obtained.

Suboperation 702b: Perform channel expansion on the first processing result, to obtain a second processing result.

The channel expansion means expanding feature channels included in the first processing result, to extract the first image feature in a plurality of dimensions. In an example, the first processing result includes one feature channel, and after the channel expansion, the second processing result includes 64 feature channels.

Suboperation 702c: Set a weight for image information of at least one region in the second processing result, to obtain a third processing result.

The at least one region is a region in a plane including the first dimension and the second dimension. In an example embodiment, the computer device divides an x-y plane in the 3D image into a plurality of regions, and sets a weight for each region. The regions may correspond to a same weight or different weights.

In an example embodiment, the computer device sets a weight for each region according to parameters of pixel points included in the each region. The parameters may be a color, a brightness, and the like. For example, when a color of pixel points included in a region is a first preset color, a weight of the region is relatively high; and when a color of pixel points included in a region is a second preset color, a weight of the region is relatively low. The first preset color refers to a color presented when a lesion occurs on a human tissue, for example, black or yellow. The second preset color refers to a color presented when no lesion occurs on a human tissue, for example, red.

In an example embodiment, the computer device sets a weight according to a position of each region on the x-y plane. For example, a position of a region on the x-y plane being closer to a center indicates a higher weight of the region; and a position of a region on the x-y plane being closer to an edge indicates a lower weight of the region.

Suboperation 702d: Perform feature extraction on the third processing result, to obtain the first image feature.

The image classification model performs feature extraction on the third processing result in which weights of regions are set, to finally obtain the first image feature.

Operation 703: Extract a second image feature corresponding to the third-dimensional image information from the 3D image.

In an example embodiment, the third-dimensional image information is z-direction image information. In an example embodiment, operation 703 includes the following suboperations:

Suboperation 703a: Perform channel expansion on the 3D image, to obtain a fourth processing result.

The channel expansion means expanding feature channels included in the 3D image, to extract the second image feature in a plurality of dimensions. A quantity of feature channels included in the fourth processing result is less than a quantity of feature channels included in the second processing result. In an example, the 3D image includes one feature channel, and after the channel expansion, the fourth processing result includes 8 feature channels.

Suboperation 703b: Set a weight for at least one channel in the fourth processing result, to obtain a fifth processing result.

The computer device sets a weight for each feature channel in the fourth processing result, to obtain the fifth processing result. The channels may correspond to a same weight or different weights. In an example embodiment, the computer device sets a weight for each channel according to a feature parameter corresponding to the each channel. In an example embodiment, the computer device includes correspondences between feature parameters and weights. After determining feature parameters corresponding to channels, the computer device searches the correspondences for weights corresponding to the channels, and then performs weight setting.

Suboperation 703c: Perform feature extraction on the fifth processing result, to obtain the second image feature.

The image classification model performs feature extraction on the fifth processing result in which the weights of the channels are set, to finally obtain the second image feature.

Operation 704: Fuse the first image feature and the second image feature, to obtain a fused image feature corresponding to the 3D image.

After the image classification model extracts the first image feature and the second image feature, the first image feature and the second image feature are fused by using a feature fusion network, to obtain the fused image feature corresponding to the 3D image.

Operation 705: Determine a classification result corresponding to the 3D image according to the fused image feature corresponding to the 3D image.

After the classifier in the image classification model classifies the fused image feature corresponding to the 3D image, a classification result corresponding to the 3D image is obtained, and then the output layer outputs the classification result. In an example embodiment, the image classification model outputs a probability that the 3D image belongs to each classification result, and a classification result corresponding to a largest probability that is greater than a preset threshold is the classification result corresponding to the 3D image. The preset threshold may be set according to an embodiment. This is not limited in an example embodiment of the disclosure.

Figure 8:
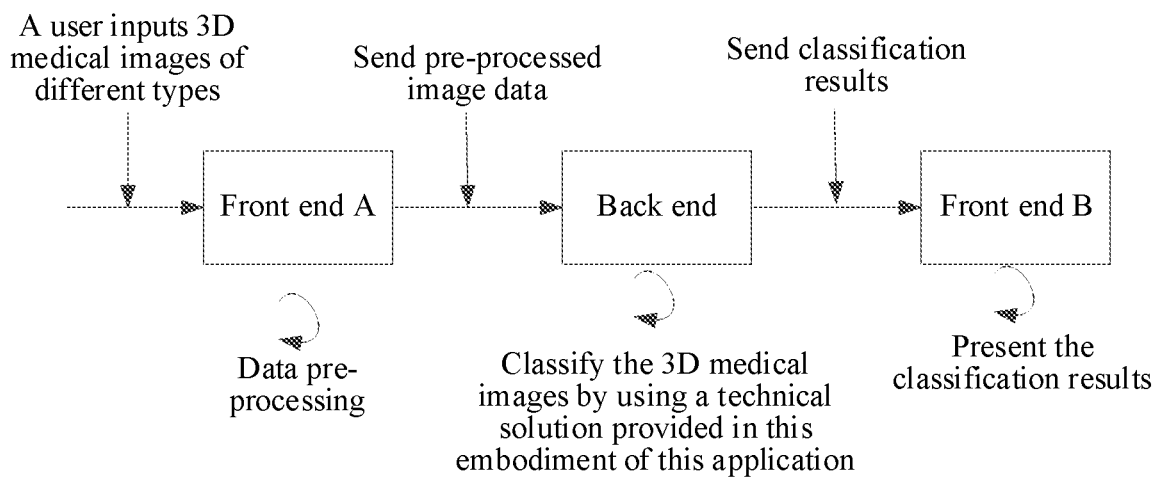
FIG. 8 is a flowchart of a 3D image classification method according to an embodiment of the disclosure.

In an illustrative example, referring to FIG. 8, a user inputs different 3D medical images of different types on a front end A. After pre-processing image data inputted by the user, the front end A sends the pre-processed image data to a back end. The back end classifies the medical images by using the technical solution provided in an example embodiment of the disclosure, and sends classification results to a front end B. The front end B presents the classification results. The front end A and the front end B may be the same front end, or may be different front ends.

Based on the above, in the technical solutions provided in an example embodiment of the disclosure, for a 3D image, an image classification model respectively extracts an image feature corresponding to planar image information (for example, x-y planar image information) including first-dimensional image information and second-dimensional image information and an image feature corresponding to third-dimensional image information (for example, z-direction image information), then fuses the two extracted features, to obtain a fused image feature, and determines a classification result corresponding to the 3D image by using the fused image feature. Compared with manually determining a classification result of a 3D image in the related art, the disclosure may improve efficiency and accuracy in image classification. In addition, because the image feature corresponding to the x-y planar image information and the image feature corresponding to the z-direction image information are respectively extracted in two manners, interference caused by different resolutions of the 3D image in different planes may be avoided. Therefore, finer and richer features are extracted, which improves accuracy in image classification.

In addition, weights are set for regions in the planar image information, and weights are set for channels in image information of a dimension, so that effective information in the 3D image may be enhanced, to improve efficiency and accuracy in image classification.

A training process of the image classification model is explained below. Operations of training the image classification model may be performed by the computer device performing the 3D image classification method, or may be performed by another computer device. This is not limited in an example embodiment of the disclosure. In an example embodiment of the disclosure, for illustrative purposes, a description is made by using an example in which the operations of training the image classification model are performed by the computer device performing the 3D image classification method.

Figure 9:
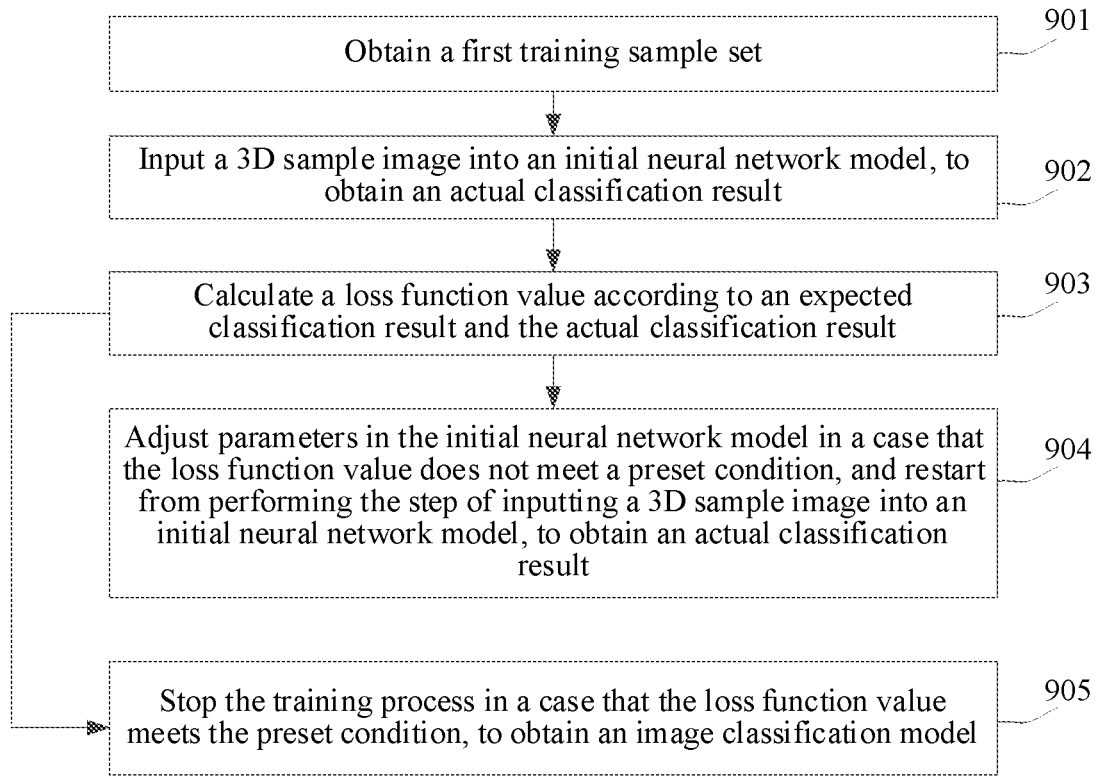
FIG. 9 is a flowchart of a training process of an image classification model according to an embodiment of the disclosure.

FIG. 9 is a flowchart of a training process of an image classification model according to an embodiment of the disclosure. Referring to FIG. 9. a training process of the image classification model may include the following operations 901-905:

Operation 901: Obtain a first training sample set.

The first training sample set includes at least one 3D sample image, the 3D sample image being annotated with an expected classification result. A quantity of the 3D sample images included in the first training sample set may be determined according to an accuracy requirement on the image classification model. A higher accuracy requirement on the image classification model indicates a larger quantity of the 3D sample images included in the first training sample set; and a lower accuracy requirement on the image classification model indicates a smaller quantity of the 3D sample images included in the first training sample set. The expected classification result may be manually annotated, or may be annotated in another manner. This is not limited in an example embodiment of the disclosure. In an example embodiment, the first training sample set may be a dataset that is provided by a hospital, that is obtained through computed tomography (CT) plain scanning, and that is used for determining causes of cerebral hemorrhage.

When the first training sample set includes a relatively small quantity of 3D sample images, data augmentation may alternatively be performed on the 3D sample images included in the first training sample set, to obtain a second training sample set. A quantity of 3D sample images included in the second training sample set is greater than the quantity of the 3D sample images included in the first training sample set. The data augmentation includes, but is not limited to, flipping, rotating, zooming, contrast enhancement, and the like.

Operation 902: Input the 3D sample image into an initial neural network model, to obtain an actual classification result.

Parameters in the initial neural network model may be randomly set. The computer device inputs the 3D sample image into an initial neural network model, and the initial neural network model outputs an actual classification result.

Operation 903: Calculate a loss function value according to the expected classification result and the actual classification result.

The computer device compares the expected classification result with the actual classification result, to obtain a loss function value.

Operation 904: Adjust parameters in the initial neural network model in a case that the loss function value does not meet a preset condition, and restart from performing the operation of inputting the 3D sample image into an initial neural network model, to obtain an actual classification result.

The preset condition may be that the loss function value is less than a preset threshold. The preset threshold may be actually determined according to an accuracy requirement on the image classification model. A higher accuracy requirement on the image classification model indicates a smaller preset threshold; and a lower accuracy requirement on the image classification model indicates a larger preset threshold.

Operation 905: Stop the training process in a case that the loss function value meets the preset condition, to obtain the image classification model.

The computer device first determines a magnitude relationship between the loss function value and the preset threshold, when the loss function value is greater than the preset threshold, updates the parameters in the initial neural network model by using a BP algorithm, and restarts from performing operation 902, until the loss function value is less than the preset threshold.

An effect of classification on the 3D image is explained below with reference to the structure of the image classification model shown in FIG. 2. The 3D image is a CT image that is used for determining causes of cerebral hemorrhage and that is provided by a hospital. Referring to Table 1, which shows parameters of some structures in the image classification model and outputted image features.

TABLE 1

|  | First subnetwork | Second subnetwork | Output size |
| --- | --- | --- | --- |
| Input layer |  |  | $30 \times 280^2$ |
| Convolutional layer 1 | Stride 6, $1^2$, $12 \times 1^2$, 1 |  | Output data of first subnetwork: $4 \times 280^2$ Output data of second subnetwork: $30 \times 280^2$ |
| Convolutional layer 2 | Stride 6, $2^2$, $1 \times 7^2$, 64 | Stride 6, $2^2$, $5 \times 7^2$, 8 | Output data of first subnetwork: $4 \times 140^2$ Output data of second subnetwork: $30 \times 140^2$ |
| Pooling layer 1 | Stride 1, $2^2$, $1 \times 3^2$, max | Stride 1, $2^2$, $1 \times 3^2$, max | Output data of first subnetwork: $4 \times 70^2$ Output data of second subnetwork: $30 \times 70^2$ |
| Block 1 | $\begin{bmatrix} 1 \times 1^2, 64 \\ 1 \times 3^2, 64 \end{bmatrix} \times 2,$ $K = 10, r = 16$ | $\begin{bmatrix} 3 \times 1^2, 8 \\ 1 \times 3^2, 8 \end{bmatrix} \times 2,$ $K = 30, r = 16$ | Output data of first subnetwork: $4 \times 70^2$ Output data of second subnetwork: $30 \times 70^2$ |
| Block 2 | $\begin{bmatrix} 1 \times 1^2, 128 \\ 1 \times 3^2, 128 \end{bmatrix} \times 2,$ $K = 7, r = 16$ | $\begin{bmatrix} 3 \times 1^2, 16 \\ 1 \times 3^2, 16 \end{bmatrix} \times 2,$ $K = 30, r = 16$ | Output data of first subnetwork: $4 \times 35^2$ Output data of second subnetwork: $30 \times 35^2$ |
| Block 3 | $\begin{bmatrix} 3 \times 1^2, 256 \\ 1 \times 3^2, 256 \end{bmatrix} \times 2,$ $K = 6, r = 16$ | $\begin{bmatrix} 3 \times 1^2, 32 \\ 1 \times 3^2, 32 \end{bmatrix} \times 2,$ $K = 30, r = 16$ | Output data of first subnetwork: $4 \times 18^2$ Output data of second subnetwork: $30 \times 18^2$ |
| Block 4 | $\begin{bmatrix} 3 \times 1^2, 512 \\ 1 \times 3^2, 512 \end{bmatrix} \times 2,$ $K = 3, r = 16$ | $\begin{bmatrix} 3 \times 1^2, 64 \\ 1 \times 3^2, 64 \end{bmatrix} \times 2,$ $K = 30, r = 16$ | Output data of first subnetwork: $4 \times 9^2$ Output data of second subnetwork: $30 \times 9^2$ |

TABLE 1-continued

| | First subnetwork | Second subnetwork | Output size |
|---|---|---|---|
| Block 5 | $\begin{bmatrix} 3\times 1^2, 1024 \\ 1\times 3^2, 1024 \end{bmatrix} \times 2,$ $K=5, r=16$ | $\begin{bmatrix} 3\times 1^2, 128 \\ 1\times 3^2, 128 \end{bmatrix} \times 2,$ $K=30, r=16$ | Output data of first subnetwork: $4 \times 5^2$ Output data of second subnetwork: $30 \times 5^2$ |

The following describes apparatus embodiments of the disclosure, which may be used for executing the method embodiments of the disclosure. For details not disclosed in the apparatus embodiments of the disclosure, reference may be made to the method embodiments of the disclosure.

Figure 10:
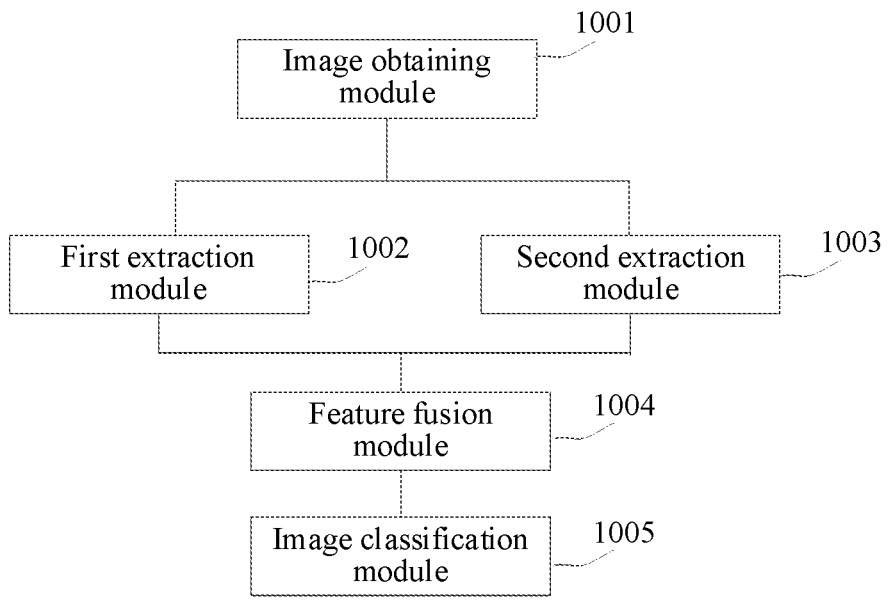
FIG. 10 is a block diagram of a 3D image classification apparatus according to an embodiment of the disclosure.

FIG. 10 is a block diagram of a 3D image classification apparatus according to an embodiment of the disclosure. The apparatus has functions of implementing the foregoing method(s) according to example embodiments. The functions may be implemented by using hardware, or may be implemented by hardware executing corresponding software. The apparatus may include: an image obtaining module 1001, a first extraction module 1002, a second extraction module 1003, a feature fusion module 1004, and an image classification module 1005.

The image obtaining module 1001 is configured to obtain a 3D image, the 3D image including first-dimensional image information, second-dimensional image information, and third-dimensional image information.

The first extraction module 1002 is configured to extract a first image feature corresponding to planar image information from the 3D image, the planar image information including the first-dimensional image information and the second-dimensional image information.

The second extraction module 1003 is configured to extract a second image feature corresponding to the third-dimensional image information from the 3D image.

The feature fusion module 1004 is configured to fuse the first image feature and the second image feature, to obtain a fused image feature corresponding to the 3D image.

The image classification module 1005 is configured to determine a classification result corresponding to the 3D image according to the fused image feature corresponding to the 3D image.

Based on the above, in the technical solutions provided in an example embodiment of the disclosure, for a 3D image, an image classification model respectively extracts an image feature corresponding to planar image information (for example, x-y planar image information) including first-dimensional image information and second-dimensional image information and an image feature corresponding to third-dimensional image information (for example, z-direction image information), then fuses the two extracted features, to obtain a fused image feature, and determines a classification result corresponding to the 3D image by using the fused image feature. Compared with manually determining a classification result of a 3D image in the related art, the disclosure may improve efficiency and accuracy in image classification. In addition, because the image feature corresponding to the x-y planar image information and the image feature corresponding to the z-direction image information are respectively extracted in two manners, interference caused by different resolutions of the 3D image in different planes may be avoided. Therefore, finer and richer features are extracted, which improves accuracy in image classification.

In an example embodiment provided based on the embodiment shown in FIG. 10, the first extraction module 1002 is configured to:
compress the third-dimensional image information in the 3D image, to obtain a first processing result;
perform channel expansion on the first processing result, to obtain a second processing result;
set a weight for image information of at least one region in the second processing result, to obtain a third processing result, the at least one region being a region in a plane including a first dimension and a second dimension; and
perform feature extraction on the third processing result, to obtain the first image feature.

In an example embodiment provided based on the embodiment shown in FIG. 10, the second extraction module 1003 is configured to:
perform channel expansion on the 3D image, to obtain a fourth processing result;
set a weight for at least one channel in the fourth processing result, to obtain a fifth processing result; and
perform feature extraction on the fifth processing result, to obtain the second image feature.

In an example embodiment provided based on the embodiment shown in FIG. 10, the classification result corresponding to the 3D image is determined by an image classification model, the image classification model including a first subnetwork, a second subnetwork, a feature fusion network, and a classifier.

The first subnetwork is configured to extract, from the 3D image, the first image feature corresponding to the planar image information including the first-dimensional image information and the second-dimensional image information.

The second subnetwork is configured to extract the second image feature corresponding to the third-dimensional image information from the 3D image.

The feature fusion network is configured to fuse the first image feature and the second image feature, to obtain the fused image feature corresponding to the 3D image.

The classifier is configured to determine the classification result corresponding to the 3D image according to the fused image feature corresponding to the 3D image.

In an example embodiment, a training process of the image classification model is as follows:
obtaining a first training sample set, the first training sample set including at least one 3D sample image, the 3D sample image being annotated with an expected classification result;
inputting the 3D sample image into an initial neural network model, to obtain an actual classification result;
calculating a loss function value according to the expected classification result and the actual classification result;
adjusting parameters in the initial neural network model in a case that the loss function value does not meet a preset condition, and restarting from performing the operation of inputting the 3D sample image into an initial neural network model, to obtain an actual classification result; and stopping the training process in a case that the loss function value meets the preset condition, to obtain the image classification model.

In an example embodiment provided based on the embodiment shown in FIG. 10, the 3D image is a medical image, and the apparatus further includes: an annotation module (not shown in FIG. 10).

The annotation module is configured to annotate pathological regions in the medical image, to obtain an annotated medical image, the annotated medical image being used for determining a classification result corresponding to the medical image.

Figure 11:
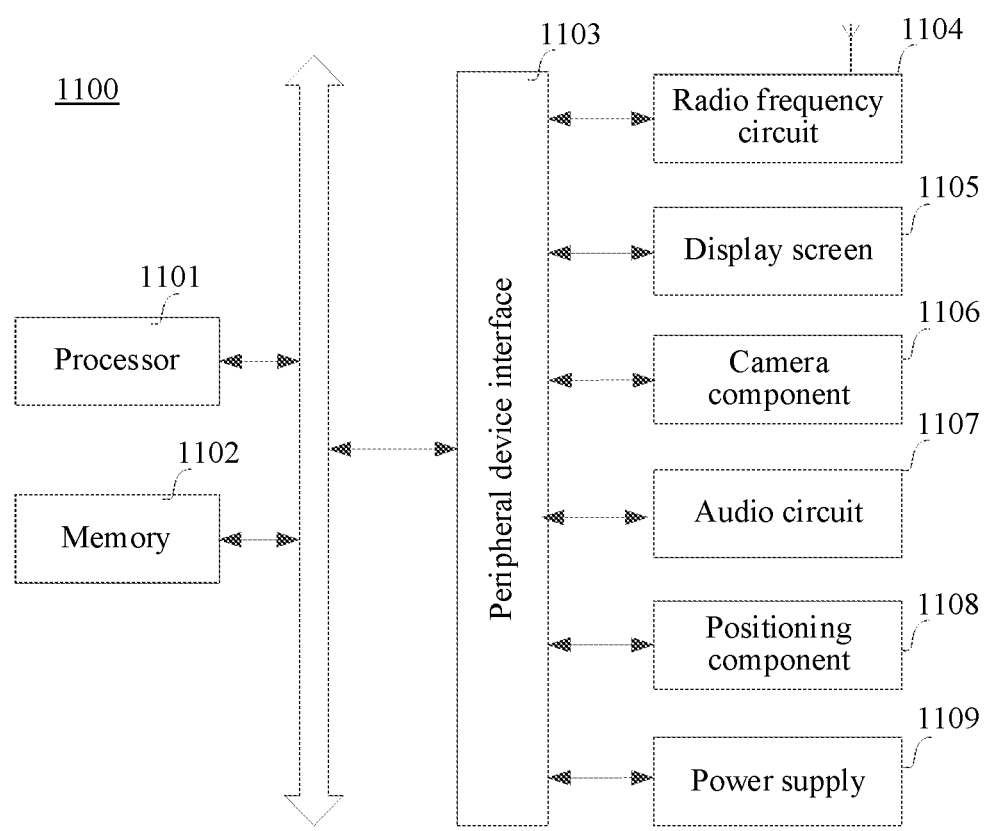
FIG. 11 is a block diagram of a computer device according to an embodiment of the disclosure.

FIG. 11 is a structural block diagram of a computer device 1100 according to an example embodiment of the disclosure. The computer device 1100 may be a smartphone, a tablet computer, a notebook computer, or a desktop computer. The computer device 1100 may also be referred to as another name such as user equipment (UE), a portable computer device, a laptop computer device, or a desktop computer device.

Generally, the computer device 1100 includes a processor 1101 and a memory 1102.

The processor 1101 may include one or more processing cores, for example, a 4-core processor or an 8-core processor. The processor 1101 may be implemented by using at least one hardware form of a digital signal processor (DSP), a field-programmable gate array (FPGA), and a programmable logic array (PLA). The processor 1101 may also include a main processor and a coprocessor. The main processor is a processor configured to process data in an awake state, and is also referred to as a central processing unit (CPU). The coprocessor is a low power consumption processor configured to process data in a standby state. In some embodiments, the processor 1101 may be integrated with a graphics processing unit (GPU). The GPU is configured to render and draw content that needs to be displayed on a display screen. In some embodiments, the processor 1101 may further include an artificial intelligence (AI) processor. The AI processor is configured to process a computing operation related to machine learning.

The memory 1102 may include one or more computer-readable storage media. The computer-readable storage medium may be non-transient. The memory 1102 may further include a high-speed random access memory and a nonvolatile memory, for example, one or more disk storage devices or flash storage devices. In some embodiments, the non-transitory computer-readable storage medium in the memory 1102 is configured to store at least one instruction, the at least one instruction being configured to be executed by the processor 1101 to implement the 3D image classification method provided in the method embodiments of the disclosure.

In some embodiments, the computer device 1100 may further include a peripheral device interface 1103 and at least one peripheral device. The processor 1101, the memory 1102, and the peripheral device interface 1103 may be connected by using a bus or a signal cable. Each peripheral device may be connected to the peripheral device interface 1103 by using a bus, a signal cable, or a circuit board. Specifically, the peripheral device includes: at least one of a radio frequency (RF) circuit 1104, a display 1105, a camera component 1106, an audio circuit 1107, a positioning component 1108, and a power supply 1109.

In some embodiments, the computer device 1100 further includes one or more sensors. The one or more sensors include, but are not limited to, an acceleration sensor, a gyroscope sensor, a pressure sensor, a fingerprint sensor, an optical sensor, and a proximity sensor.

A person skilled in the art would understand that the structure shown in FIG. 11 does not constitute any limitation on the computer device 1100, and the computer device may include more components or fewer components than those shown in the figure, or some components may be combined, or a different component deployment may be used.

In an example embodiment, a computer-readable storage medium is further provided, the storage medium storing at least one instruction, at least one program, a code set, or an instruction set, the at least one instruction, the at least one program, the code set, or the instruction set being loaded and executed by a processor of an electronic device to implement the foregoing 3D image classification method.

In an example embodiment, the computer-readable storage medium may be a read-only memory (ROM), a RAM, a magnetic tape, a floppy disk, an optical data storage device, or the like.

In an example embodiment, a computer program product is further provided, when executed, the computer program product is used for performing the foregoing 3D image classification method.

It is to be understood that "plurality of" mentioned in the specification means two or more. "And/or" describes an association relationship for associated objects and represents that three relationships may exist. For example, A and/or B may represent the following three cases: only A exists, both A and B exist, and only B exists. The character "/" generally indicates an "or" relationship between the associated objects. The "first", the "second" and similar terms used herein do not indicate any order, quantity or significance, but are used to only distinguish different components.

The sequence numbers of the foregoing embodiments of the disclosure are merely for description purpose but do not imply the preference among the embodiments.

The technical solutions provided in the embodiments of the disclosure achieve at least the following beneficial effects.

For a 3D image, an image classification model respectively extracts an image feature corresponding to planar image information (for example, x-y planar image information) including first-dimensional image information and second-dimensional image information and an image feature corresponding to third-dimensional image information (for example, z-direction image information), then fuses the two extracted features, to obtain a fused image feature, and determines a classification result corresponding to the 3D image by using the fused image feature. Compared with manually determining a classification result of a 3D image in the related art, the disclosure may improve efficiency and accuracy in image classification.

At least one of the components, elements, modules or units described herein may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in some of block diagrams, communication between the components, elements or units may be performed through the bus. Functional aspects of the above exemplary embodiments may be implemented in algorithms that execute on one or more processors. Furthermore, the components, elements or units represented by a block or processing operations may employ any number of related art techniques for electronics configuration, signal processing and/or control, data processing and the like.

The foregoing descriptions are merely example embodiments of the disclosure, but are not intended to limit the disclosure. Any modification, equivalent replacement, or improvement made without departing from the spirit and principle of the disclosure shall fall within the protection scope of the disclosure.

What is claimed is:

1. A three-dimensional (3D) image classification method, performed by a computer device, the method comprising:
    obtaining a 3D image, the 3D image comprising image information of a first dimension, image information of a second dimension, and image information of a third dimension, wherein the first dimension, the second dimension, and the third dimension are respectively represented by X, Y, and Z in a 3D coordinate system;
    extracting a first image feature corresponding to planar image information from the 3D image, the planar image information corresponding to at least one region in a plane comprising the first dimension and the second dimension;
    extracting, from the 3D image, a second image feature corresponding to the image information of the third dimension;
    fusing the first image feature and the second image feature, to obtain a fused image feature; and
    determining a result of classifying the 3D image according to the fused image feature.

2. The method according to claim 1, wherein the extracting the first image feature comprises:
    compressing the image information of the third dimension in the 3D image, to obtain a first processing result;
    performing channel expansion on the first processing result, to obtain a second processing result;
    setting a weight for the planar image information of the at least one region in the second processing result, to obtain a third processing result; and
    performing feature extraction on the third processing result, to obtain the first image feature.

3. The method according to claim 2, wherein the setting the weight comprises:
    setting the weight for the at least one region according to a parameter of a pixel point included in the at least one region, the parameter comprising at least one of a color or a brightness.

4. The method according to claim 2, wherein the setting the weight comprises:
    sets the weight for the at least one region according to a position of the at least one region on the plane.

5. The method according to claim 1, wherein the extracting the second image feature comprises:
    performing channel expansion on the 3D image, to obtain a fourth processing result;
    setting a weight for at least one channel in the fourth processing result, to obtain a fifth processing result; and
    performing feature extraction on the fifth processing result, to obtain the second image feature.

6. The method according to claim 5, wherein the setting the weight comprises:
    determining at least one feature parameter of the at least one channel, and by using preset correspondences between feature parameters and weights and the determined at least one feature parameter, setting the weight for the at least one channel.

7. The method according to claim 1, wherein the result of classifying the 3D image is determined by an image classification model, the image classification model comprising a first subnetwork, a second subnetwork, a feature fusion network, and a classifier,
    the first subnetwork being configured to extract the first image feature corresponding to the planar image information from the 3D image;
    the second subnetwork being configured to extract the second image feature corresponding to the image information of the third dimension from the 3D image;
    the feature fusion network being configured to fuse the first image feature and the second image feature, to obtain the fused image feature; and
    the classifier being configured to determine the result of classifying the 3D image according to the fused image feature.

8. The method according to claim 7, wherein the image classification model is trained by:
    (a) obtaining a first training sample set, the first training sample set comprising at least one 3D sample image, the 3D sample image being annotated with an expected classification result;
    (b) inputting the 3D sample image into an initial neural network model, to obtain an actual classification result;
    (c) calculating a loss function value according to the expected classification result and the actual classification result;
    (d) adjusting parameters in the initial neural network model based on the loss function value not meeting a preset condition, and performing operations (a)-(c) with the adjusted parameters; and
    (e) stopping training of the image classification model based on the loss function value meeting the preset condition, to obtain the image classification model.

9. The method according to claim 1, wherein the 3D image is a medical image, and after the obtaining the 3D image, the method further comprises:
    annotating a pathological region in the medical image, to obtain an annotated medical image, the annotated medical image being used for determining a result of classifying the medical image.

10. A computer device, comprising a processor and a memory, the memory storing at least one instruction, the at least one instruction being loaded and executed by the processor to implement the 3D image classification method according to claim 1.

11. A three-dimensional (3D) image classification apparatus, comprising:
at least one memory configured to store program code; and
at least one processor configured to read the program code and operate as instructed by the program code, the program code comprising:
image obtaining code configured to cause the at least one processor to obtain a 3D image, the 3D image comprising image information of a first dimension, image information of a second dimension, and image information of a third dimension, wherein the first dimension, the second dimension, and the third dimension are respectively represented by X, Y, and Z in a 3D coordinate system;
first extraction code configured to cause the at least one processor to extract a first image feature corresponding to planar image information from the 3D image, the planar image information corresponding to at least one region in a plane comprising the first dimension and the second dimension;
second extraction code configured to cause the at least one processor to extract, from the 3D image, a second image feature corresponding to the image information of the third dimension;
feature fusion code configured to cause the at least one processor to fuse the first image feature and the second image feature, to obtain a fused image feature; and
image classification code configured to cause the at least one processor to determine a result of classifying the 3D image according to the fused image feature.

12. The apparatus according to claim 11, wherein the first extraction code comprises:
compression sub-code configured to cause the at least one processor to compress the image information of the third dimension in the 3D image, to obtain a first processing result;
first channel expansion sub-code configured to cause the at least one processor to perform channel expansion on the first processing result, to obtain a second processing result;
first weight setting sub-code configured to cause the at least one processor to set a weight for the planar image information of the at least one region in the second processing result, to obtain a third processing result; and
first feature extraction sub-code configured to cause the at least one processor to perform feature extraction on the third processing result, to obtain the first image feature.

13. The apparatus according to claim 12, wherein the first weight setting sub-code is configured to cause the at least one processor to set the weight for the at least one region according to a parameter of a pixel point included in the at least one region, the parameter comprising at least one of a color or a brightness.

14. The apparatus according to claim 12, wherein the first weight setting sub-code is configured to cause the at least one processor to set the weight for the at least one region according to a position of the at least one region on the plane.

15. The apparatus according to claim 11, wherein the second extraction code comprises:
second channel expansion sub-code configured to cause the at least one processor to perform channel expansion on the 3D image, to obtain a fourth processing result;
second weight setting sub-code configured to cause the at least one processor to set a weight for at least one channel in the fourth processing result, to obtain a fifth processing result; and
second feature extraction sub-code configured to cause the at least one processor to perform feature extraction on the fifth processing result, to obtain the second image feature.

16. The apparatus according to claim 15, wherein the second weight setting sub-code configured to cause the at least one processor to determine at least one feature parameter of the at least one channel, and by using preset correspondences between feature parameters and weights and the determined at least one feature parameter, set the weight for the at least one channel.

17. The apparatus according to claim 11, wherein the image classification code is configured to cause the at least one processor to determine the result of classifying the 3D image by an image classification model, the image classification model comprising a first subnetwork, a second subnetwork, a feature fusion network, and a classifier,
the first subnetwork being configured to extract the first image feature corresponding to the planar image information from the 3D image;
the second subnetwork being configured to extract the second image feature corresponding to the image information of the third dimension from the 3D image;
the feature fusion network being configured to fuse the first image feature and the second image feature, to obtain the fused image feature; and
the classifier being configured to determine the result of classifying the 3D image according to the fused image feature.

18. The apparatus according to claim 17, wherein the image classification model is trained by:
(a) obtaining a first training sample set, the first training sample set comprising at least one 3D sample image, the 3D sample image being annotated with an expected classification result;
(b) inputting the 3D sample image into an initial neural network model, to obtain an actual classification result;
(c) calculating a loss function value according to the expected classification result and the actual classification result;
(d) adjusting parameters in the initial neural network model based on the loss function value not meeting a preset condition, and performing operations (a)-(c) with the adjusted parameters; and
(e) stopping training of the image classification model based on the loss function value meeting the preset condition, to obtain the image classification model.

19. The apparatus according to claim 11, wherein the 3D image is a medical image, and the program code further comprises:
annotation configured to cause the at least one processor to annotate a pathological region in the medical image, to obtain an annotated medical image, the annotated medical image being used for determining a result of classifying the medical image.

20. A non-transitory computer-readable storage medium, storing at least one instruction, the at least one instruction being loaded and executed by a processor to perform:
obtaining a 3D image, the 3D image comprising image information of a first dimension, image information of a second dimension, and image information of a third dimension, wherein the first dimension, the second dimension, and the third dimension are respectively represented by X, Y, and Z in a 3D coordinate system;

extracting a first image feature corresponding to planar image information from the 3D image, the planar image information corresponding to at least one region in a plane comprising the first dimension and the second dimension;

extracting, from the 3D image, a second image feature corresponding to the image information of the third dimension;

fusing the first image feature and the second image feature, to obtain a fused image feature; and determining a result of classifying the 3D image according to the fused image feature.

* * * * *